(12) United States Patent  
Nemoto

(10) Patent No.: US 7,699,785 B2  
(45) Date of Patent: Apr. 20, 2010

(54) METHOD FOR DETERMINING SLEEP STAGES

(75) Inventor: Shin Nemoto, Kashiwa (JP)

(73) Assignee: Sleep System Laboratory Inc., Kashiwa-Shi (JP)

( * ) Notice: Subject to any disclaimer, the term of this patent is extended or adjusted under 35 U.S.C. 154(b) by 338 days.

(21) Appl. No.: 10/590,058

(22) PCT Filed: Feb. 23, 2005

(86) PCT No.: PCT/JP2005/003412

§ 371 (c)(1),  
(2), (4) Date: Aug. 21, 2006

(87) PCT Pub. No.: WO2005/082252

PCT Pub. Date: Sep. 9, 2005

(65) Prior Publication Data

US 2008/0039736 A1 Feb. 14, 2008

(30) Foreign Application Priority Data

Mar. 1, 2004 (JP) ............................. 2004-056538

(51) Int. Cl.  
*A61B 5/02* (2006.01)  
*A61B 5/00* (2006.01)  
*A61B 5/04* (2006.01)

(52) U.S. Cl. ...................... 600/483; 600/481; 600/500; 600/509; 600/513; 600/485; 600/300

(58) Field of Classification Search .................. 600/300, 600/301, 481, 483–486, 488, 490–503, 508–526  
See application file for complete search history.

(56) References Cited

U.S. PATENT DOCUMENTS

| | | | |
|---|---|---|---|
| 4,977,896 A * | 12/1990 | Robinson et al. | 600/409 |
| 5,101,831 A * | 4/1992 | Koyama et al. | 600/500 |
| 5,247,939 A * | 9/1993 | Sjoquist et al. | 600/510 |
| 5,269,325 A * | 12/1993 | Robinson et al. | 600/409 |
| 6,689,064 B2 * | 2/2004 | Hager et al. | 600/454 |
| 7,094,207 B1 * | 8/2006 | Koh | 600/529 |
| 7,189,204 B2 * | 3/2007 | Ni et al. | 600/300 |

(Continued)

FOREIGN PATENT DOCUMENTS

JP   A 2000-325315   11/2000

(Continued)

OTHER PUBLICATIONS

Hiroyuki Inabe et al., "The relationship between heart rate variability and sleep state (2)", 11$^{th}$ Symposium on Human Interface, pp. 263-266, Kyoto, Oct. 18-20, 1995.

*Primary Examiner*—Charles A Marmor, II  
*Assistant Examiner*—Navin Natnithithadha  
(74) *Attorney, Agent, or Firm*—Oliff & Berridge, PLC

(57) ABSTRACT

The present invention provides a method for determining sleep stages of an examinee, including detecting signals of the examinee with a biosignal detector, calculating a signal strength deviation value that indicates deviation of a signal strength of the detected signals, and determining a sleep stage by using the signal strength deviation value or a value of a plurality of values based on the signal strength deviation value as an indicator value.

7 Claims, 6 Drawing Sheets

U.S. PATENT DOCUMENTS

| | | | |
|---|---|---|---|
| 7,221,975 B2 * | 5/2007 | Lindstrom | 600/509 |
| 7,225,021 B1 * | 5/2007 | Park et al. | 607/18 |
| 7,252,640 B2 * | 8/2007 | Ni et al. | 600/538 |
| 7,308,309 B1 * | 12/2007 | Koh | 607/17 |
| 7,310,551 B1 * | 12/2007 | Koh et al. | 600/523 |
| 7,316,171 B2 * | 1/2008 | Nemoto | 73/866.1 |
| 7,460,900 B1 * | 12/2008 | Gill et al. | 600/509 |
| 2003/0069505 A1 * | 4/2003 | Hager et al. | 600/454 |
| 2003/0153953 A1 * | 8/2003 | Park et al. | 607/17 |
| 2003/0153954 A1 * | 8/2003 | Park et al. | 607/17 |
| 2004/0002742 A1 * | 1/2004 | Florio | 607/19 |
| 2004/0111041 A1 * | 6/2004 | Ni et al. | 600/544 |
| 2005/0148897 A1 * | 7/2005 | Cho et al. | 600/533 |
| 2006/0042409 A1 * | 3/2006 | Nemoto | 73/866.1 |

FOREIGN PATENT DOCUMENTS

| | | |
|---|---|---|
| JP | A 2001-61820 | 3/2001 |
| JP | A 2002-219116 | 8/2002 |
| JP | A 2004-49838 | 2/2004 |
| JP | A 2004-358179 | 12/2004 |

* cited by examiner

|  | Awake/REM | Shallow | Deep | Coincidence |
|---|---|---|---|---|
| Conventional System | 25.7% | 61.7% | 12.5% | 86.5% |
| Present System | 24.6% | 49.3% | 26.1% | |

METHOD FOR DETERMINING SLEEP STAGES

This application is the U.S. National Stage of PCT/JP2005/003412, filed Feb. 23, 2005, which claims priority from JP 2004-056538, filed Mar. 1, 2004, the disclosures of which are incorporated herein in their entireties by reference thereto.

BACKGROUND

The present invention relates to a method for determining sleep stages of an examinee from biosignals detected by a biosignal detector, which is readily handled and can be routinely used.

A sleep state is often examined as an indicator for determining the health condition of an individual. It is well-known that sleep and health are closely associated. Health and sleep depth and quality of sleep during the night are closely associated with mood and vigor on the following day. Meanwhile, during periods of mental stress or sickness, comfortable sleep is not obtained because the depth of sleep and the transition pattern of sleep stages are changed.

During healthy sleep, non-REM sleep and REM sleep repeatedly appear at a constant interval after falling asleep. It has been known that sleep rhythm is disturbed during periods of sickness or mental stress. Therefore, it becomes possible to know the mental stress level and poor physical condition of examinees by monitoring sleep stages and their occurrence pattern while the examinees sleep.

In particular, the elderly often complain of a sleep state disorder such as shallow sleep, and have a problem in sleep quality. By examining the transition of sleep stages to understand sleep quality, it becomes possible to find ways of addressing the problem in sleep quality, and find measures to improve sleep quality.

A conventional method for examining sleep stages is a the method using a sleep polysomnogram (PSG). In the method using PSG, a significant amount of information can be obtained by estimating the activity of the cerebral nervous system during sleep from brain waves, myoelectric potential and eye movements. However, it is difficult to obtain natural sleep because the measurement is performed by mounting many electrodes on the face and the body of an examinee, and a period of several days to a week is required for growing accustomed to this method. Therefore, physical and bodily loads given to the examinee are extremely heavy, and further, it is necessary that this measurement is performed in a special facility such as a hospital by an expert who is familiarized with the handling. Therefore, the cost required for this method becomes expensive.

Due to these circumstances, although it can be an effective therapy to use PSG for patients with an obvious sleep disorder, it is difficult to use PSG for routine health care.

Thus, methods for simply examining sleep stages without using PSG for examining the daily health state of the examinee have been proposed. For example, a method for determining the sleep stages by wearing a wristwatch type vibration strength measurement device on an arm and measuring its acceleration is available, but only two sleep stages, e.g., REM sleep and non-REM sleep can be detected. For health care use, however, it is necessary to detect at least three stages, i.e., the awake/REM sleep stage, the shallow non-REM sleep stage and the deep non-REM sleep stage. Thus, because this type of non-PSG device only detects two sleep stages, it is unsuitable for purposes of health care.

Another proposed method for determining sleep stages is a method for non-invasively measuring a heartbeat rate, and determining sleep stages from the measured heartbeat rate signal data (e.g., see Japanese Published Unexamined Patent Application 2000-325315). This method is capable of examining four sleep stages, e.g., the awake state, REM sleep, shallow non-REM sleep and deep non-REM sleep. Therefore, it is possible to use this method for health care. However, complicated calculations, calculation time and large memory are required because the sleep stages are determined by extracting heartbeat signals from non-invasively detected biosignals and analyzing the effect of the autonomic nerve from the heartbeat signals. As a result, the configuration of the device implementing this method becomes complicated, the device becomes more expensive, and thus, it is difficult to routinely use the device.

Thus, the present invention aims at providing a method for determining the sleep stages, which is readily handled even by the elderly and can be routinely used without physically or mentally burdening an examinee.

Furthermore, the present invention aims at providing a device realized by the method of the present invention, which is inexpensive in terms of price and maintenance costs and is readily introduced.

SUMMARY

In light of the foregoing circumstances, the present invention has been made to solve, at least, the identified problems. Specifically, the present invention is characterized in that sleep stages are determined by detecting signals of an examinee with a biosignal detector, calculating a signal strength deviation value that indicates deviation of a signal strength of the signals detected by a biosignal detector, and using the signal strength deviation value or the value of the plurality of values based on the signal strength deviation value as an indicator.

As such, the present invention makes it is possible to readily determine sleep stages while keeping the price and the maintenance cost inexpensive.

The indicator value can be characterized by the signal strength data deviation value of the detected data that is detected in a predetermined time period.

Thus, the present invention makes it is possible to provide a simple method for determining sleep stages.

The indicator value can also be characterized by a signal of a difference between the signal strength data deviation value of the detected data that is detected in the predetermined time period and a moving average of the signal strength deviation value.

Accordingly, the present invention makes it is possible to make a method for determining sleep stages that can be routinely used.

The above indicator value can also be characterized by a signal of the moving average that is calculated for the signal strength deviation value of the detected data that is detected in the predetermined time period.

Thus, the present invention makes it is possible to make a method for determining sleep stages that can be routinely used, and remove a high frequency component in the signals and obtain a reasonable determination result.

The method can also be characterized in that the signal strength deviation signal value obtained by removing abnormal values from the signal strength deviation values or the value of the plurality of values based on this signal strength deviation value is used as the indicator value.

As such, the present invention makes it is possible to remove the abnormal values caused by rolling over, etc., and obtain reasonable sleep stage determination results.

The signal strength can be characterized by being the signal strength obtained as a reciprocal of a coefficient obtained by gain control of the signals detected by the biosignal detector.

Thus, the present invention makes it is possible to obtain reasonable sleep stage determination results.

The biosignal detector is characterized by being a non-invasive detector.

As such, the present invention makes it is possible to reduce the mental load.

The biosignal detector is composed of a pressure detection tube, a pressure detection sensor and a biosignal extractor, and is characterized in that the biosignal is extracted from pressure variation detected by the pressure detection sensor.

Accordingly, the present invention makes it is possible to make the price and the maintenance cost inexpensive, while keeping the handling and the measurement simple.

The biosignal detector is further characterized by being a heartbeat signal detector such as an electrocardiograph equipment and/or a pulse rate meter.

As such, the present invention makes it is possible to readily perform a measurement even by using typical measurement equipment.

The conventional methods for examining sleep stages mentioned previously, such as the common method implementing a sleep polysomnogram (PSG) and the methods for examining sleep stages without PSG have disadvantages in that the PSG method is difficult to use for routine health care, and the methods for simply examining sleep stages without PSG have a problem in terms of performance and cost.

The sleep stage detection method of the present invention is focused on the relationship between the depth of sleep in the sleep stages and the deviation in the biosignal strength. Specifically, as the depth of sleep increases in the sleep stages, the smaller the deviation becomes in the biosignal strength, and the present invention determines the sleep stage by the value of the deviation degree in the signal strength. In particular, only the measurement of the signal strength of the heartbeat signal has enabled the measurement of the sleep stage.

As a result, according to the method of the present invention, it becomes possible to realize the measurement of sleep stages, which is readily handled and can be routinely used.

Furthermore, since the measurement method is concise, the price and the maintenance costs are inexpensive. The method of the present invention realizes a readily-introducible device capable of determining the sleep stages.

DETAILED DESCRIPTION OF EMBODIMENTS

The sleep stage detection method of the present invention focuses on the relationship between the deviation of the strength of biosignals during sleep and the sleep stages. Particularly, the present invention focuses on the observation that the deeper the sleep becomes in the sleep stages, the smaller the deviation of the biosignal strength becomes.

Figure 1:
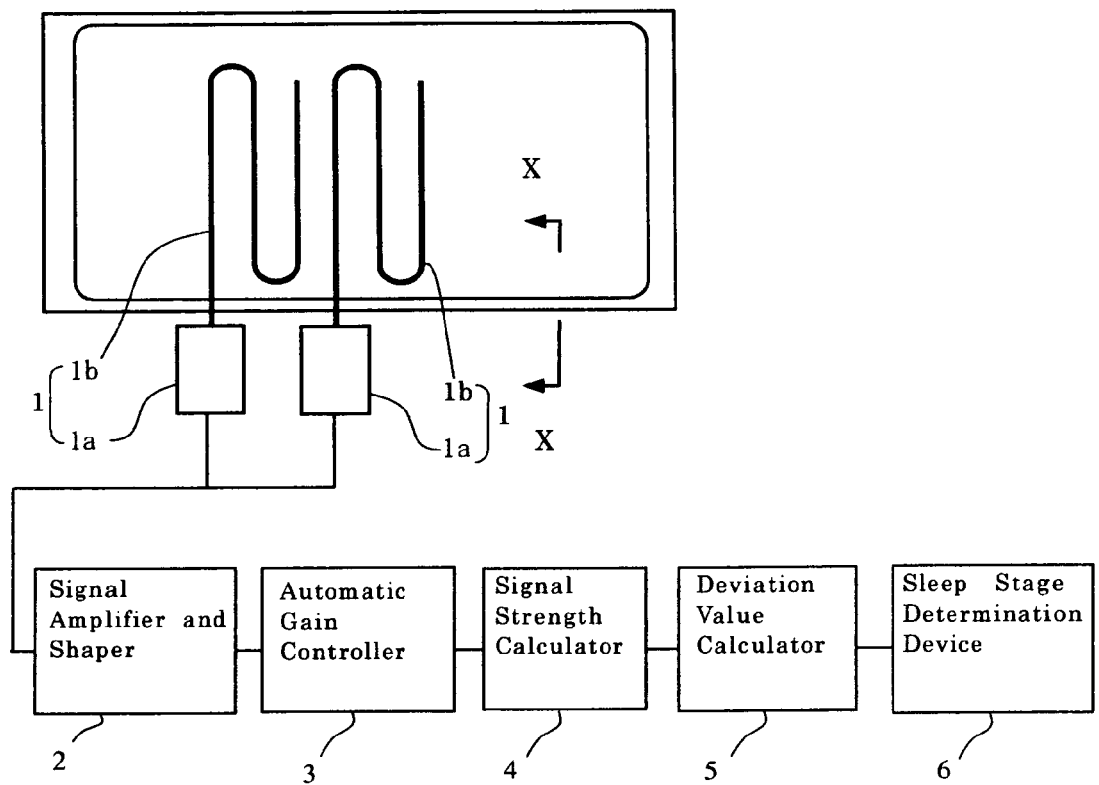
FIG. 1(A) and FIG. 1(B) show a device and a block diagram showing a flow to determine a sleep stage and a partial sectional view seen from a direction indicated by arrows, respectively, in a method for determining sleep stages of the present invention.
Figure 1:
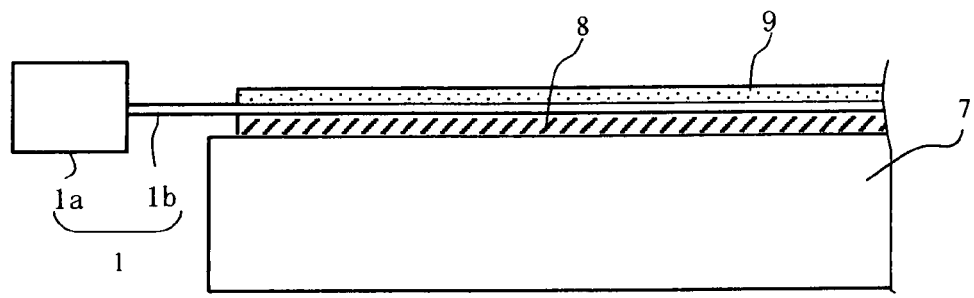

FIG. 1(A) shows a device and a block diagram for performing the method for determining sleep stages of the present invention, and FIG. 1(B) shows a partial sectional view of the device seen from a direction X. Biosignal detector 1 shown in FIGS. 1(A) and 1(B) is a non-invasive sensor, which detects fine biosignals produced by the examinee during sleep. The biosignals detected by the biosignal detector 1 are amplified by a signal amplifier and shaper 2 so that the signals can be treated in a subsequent treatment step, and unnecessary signals such as those derived from breathing are removed through a band pass filter, etc.

The biosignal detector 1 is composed of a pressure sensor 1a and a pressure detection tube 1b, and constitutes the non-invasive biosignal detector. The pressure sensor 1a is a sensor that detects fine changes in pressure. A condenser microphone type for low frequency is used as the pressure sensor 1, yet the pressure sensor 1a is not limited thereto and may be a device having an appropriate resolution power and dynamic range.

In the condenser microphone for low frequency, a property in the low frequency range has been widely enhanced by providing a chamber behind a pressure-receiving face, whereas a common sound microphone is not considered for the low frequency region. This is suitable for detecting the fine pressure variation in the pressure detection tube 1b. The condenser microphone is excellent in measuring a fine differential pressure, has the resolution power of 0.2 Pa and the dynamic range of about 50 Pa, performs much better when compared with a typically used fine differential pressure sensor utilizing ceramics, and is suitable for detecting fine pressure added to the pressure detection tube 1b by the biosignals through the body surface. A frequency property shows a nearly flat output value between 0.1 Hz to 20 Hz and is suitable for detecting fine biosignals derived from a heartbeat and respiratory rate of the examinee.

A material having a proper elastic force is used for the pressure detection tube 1b so that the internal pressure undergoes a change in response to a pressure variation range of the biosignals. In order to transmit the pressure change to the pressure sensor 1a at an appropriate response speed, it is necessary to appropriately select a volume of a hollow portion in the tube. When the pressure detection tube 1b cannot simultaneously satisfy the proper elasticity and the hollow portion volume, the volume of the hollow portion can be made appropriate by loading a core rod with an appropriate thickness in the hollow portion of the pressure detection tube 1b over a whole length of the tube.

Furthermore, the pressure detection tube 1b is disposed on a hard sheet 8 spread on a bed 7, an elastic cushion sheet 9 is spread thereon, and the examinee lies still on the pressure detection tube 1b. A position of the pressure detection tube 1b may be stabilized by incorporating the pressure detection tube 1b into the cushion sheet 9, etc.

As shown in FIG. 1a, two biosignal detectors 1 are provided. The two biosignal detectors 1 are constituted to detect the biosignals regardless of the posture of the examinee during sleep by detecting the biosignals at a chest site by one detector and detecting the biosignals at a hip site by the other detector.

The biosignals detected by the biosignal detector 1 are the mixed signals with various vibrations produced by the human body, and include the signals derived from heartbeat signals, respiratory signals and signals of rolling over. The respiratory signals are sometimes discontinued due to apneustic breathing during sleep. Thus, in the present invention, the biosignals in which the respiratory signals have been removed are taken out by the signal amplifier and shaper 2 using a filter and a device such as a statistical treatment device. These signals include the extremely high-level signals due to the rolling over.

The heartbeat signals were extracted from the signals detected by the non-invasive biosignal detector 1, but the detector is not limited thereto, and it is possible to obtain the heartbeat signals by wearing a specific heartbeat meter or detecting pulses.

An automatic gain controller 3 is a so-called AGC circuit that automatically performs gain control so that the output from the signal amplifier and shaper 2 falls within the range of the predetermined signal level. A value (coefficient) of the gain at that time is outputted to a signal strength calculator 4. In the gain control, for example, the gain is set so that amplitude of the output signals becomes small when a peak value of the signals exceeds an upper limit threshold, and the gain is set so that the amplitude becomes large when the peak value is below a lower limit threshold.

The signal strength calculator 4 calculates the signal strength from the coefficient of the gain control given to the biosignals by the automatic gain controller 3. The value of the gain obtained from the above-described AGC circuit is set so as to be small when the signal size is large and so as to be large when the signal size is small. Thus, to indicate the signal strength using the value of the gain, a function that indicates the signal strength to be in inverse proportion to the value of the gain may be set.

For the data of the signal strength obtained by the signal strength calculator 4, a standard deviation that indicates the deviation of the data for the predetermined time period is calculated in deviation value calculator 5. That is, when at a certain time, the indicator that indicates the deviation of the data sampled for a certain time until that time is referred to as the deviation value, the standard deviation is employed as the deviation value.

Further, the standard deviation was employed as the deviation value, which is the indicator that indicates the deviation, but the deviation value is not limited thereto, and for example, statistical quantities such as a variance, sum of squared deviation and range may be employed.

Finally, the sleep stage is determined by sleep stage determination device 6. The value of the standard deviation that is the deviation value of the signal strength calculated by the deviation value calculator 5 or the value derived from the standard deviation is used as an indicator signal. The threshold of the sleep stage is calculated in advance, and the sleep stage is then determined by comparing the value of the indicator signal with the value of the threshold.

Figure 2:
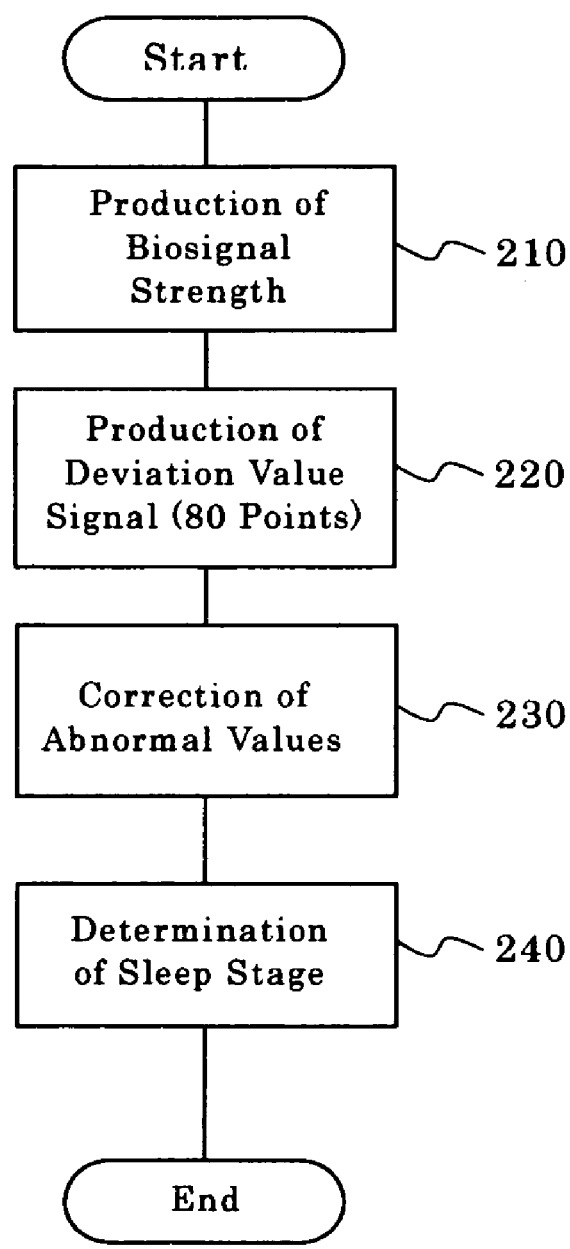
FIG. 2 shows a flowchart illustrating a procedure to determine a sleep stage in a first exemplary embodiment.

FIG. 2 shows a flowchart illustrating a procedure of the first embodiment to determine the sleep stage from the biosignal strength.

First, the value of the signal strength is calculated every predetermined time period, such as one second, by the signal strength calculator 4 to output the value into the deviation value calculator 5 (step 210). The standard deviation of the data for 80 consecutive points at each time point is calculated to obtain the deviation value signal (step 220).

Abnormal values are corrected for the deviation value by the sleep stage determination device 6 (step 230). The value of the output from the signal strength calculator 4 becomes abnormally high in some cases compared with other values of the output. For example, upon rolling over, the value of the signal strength becomes high only at that point. When the deviation value of the data including such a case is calculated, the resulting value becomes largely separated from the value in normal cases.

As a method for removing the abnormal value of the signal strength, it is desirable to employ a value not largely separated from the data immediately before if there is a value that is equal to or greater than the defined value. When the value that is equal to or greater than the defined value appears, the effect of the abnormal value on the determination of the sleep stage is excluded by replacing the value with the data within the defined values that are present immediately before it.

The abnormal value of the signal strength does not frequently appear during sleep in one night, and it is also possible to omit the abnormal value depending on the number of samples used for the calculation of the standard deviation.

Then, the sleep stage is determined by the sleep stage determination device 6 (step 240). When the sleep stage is determined, a first threshold to distinguish the awake/REM sleep from the shallow non-REM sleep and a second threshold to distinguish the shallow non-REM sleep from the deep non-REM sleep are set up, and from the two thresholds, it is determined which range the value of the deviation value signal that indicates the deviation falls into.

A finding that the above deviation value and power density of the sympathetic nerve are in a relationship of substantial proportion has been obtained. The power density value is obtained by analyzing a frequency at a certain zone (about 0.04 Hz to about 0.15 Hz) of an RR interval of an R-wave in a heartbeat, and means that as the value is increased, the activity of the sympathetic nerve is facilitated, causing the mind and body to reach an excited state, and thus, preventing a deep sleep state.

Furthermore, a finding that the above deviation value and a component ratio of a δ-wave (about 0.5 Hz to about 3.5 Hz) in brain wave components (α-wave, β-wave, θ-wave and δ-wave) obtained from the brain wave are in a relationship of substantial inverse proportion has been obtained. And, the component ratio of the δ-wave is characterized by becoming large if the sleep is deepened.

The above deviation value becomes smaller in the order of the awake/REM sleep stage, the shallow non-REM sleep stage and the deep non-REM sleep stage, and the deviation is larger in the awake/REM sleep stage and is smaller in the deep non-REM sleep stage. Therefore, the value of the second threshold to distinguish the shallow non-REM sleep from the deep non-REM sleep is smaller than the value of the first threshold to distinguish the awake/REM sleep from the shallow non-REM sleep.

As the method for obtaining the first threshold and the second threshold, it is suitable to establish the first threshold and the second threshold so that the coincidence becomes the highest compared with the determination of the sleep stages by PSG.

When the value of the deviation value signal is larger than the first threshold, the stage is determined as the wake/REM sleep stage. Meanwhile, when the value of the deviation value signal is smaller than the second threshold, the stage is determined as the deep non-REM sleep stage. The other cases are determined as the shallow non-REM sleep stage. The data of the continuous sleep stages are obtained by performing the above determination at each time.

Figure 3:
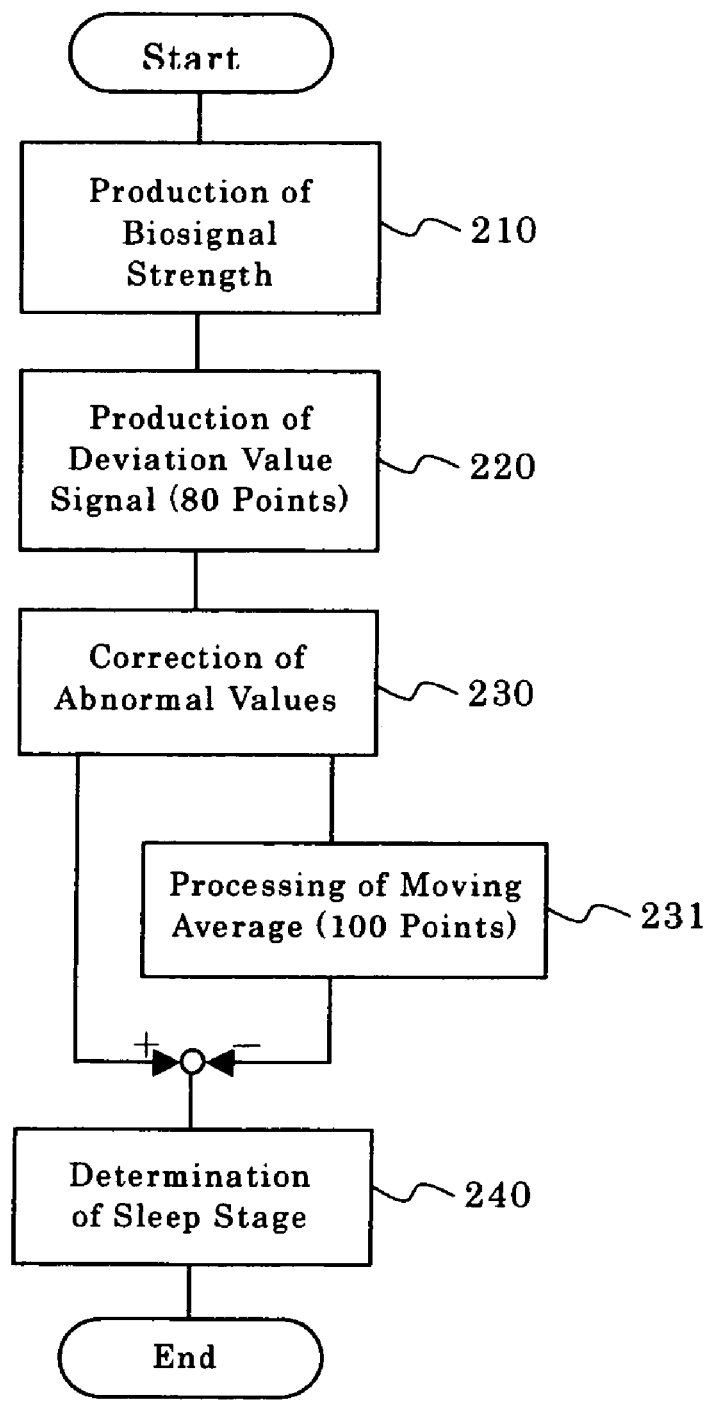
FIG. 3 shows a flowchart illustrating a procedure to determine a sleep stage in a second exemplary embodiment.

FIG. 3 shows a flowchart illustrating the procedure of the second embodiment to determine the sleep stages from the biosignal strength. The second embodiment is similar to the first embodiment in that it employs the same steps 210, 220, 230 and 240, and is different from the first embodiment in that the moving average of the standard deviation is calculated, and the value obtained by subtracting the calculated value from the value of the standard deviation is used as the deviation value signal.

For the deviation value obtained by the deviation value calculator 5, the moving average value for 100 consecutive points at each time is calculated (step 231). The difference between the deviation value obtained by the deviation value calculator 5 and the moving average value is used as the indicator value signal.

Then, using the indicator value signal, the sleep stage is determined in the same way as in the first embodiment (step 240). It is also possible to select whether the correction of the abnormal value is performed or not, if necessary.

Figure 4:
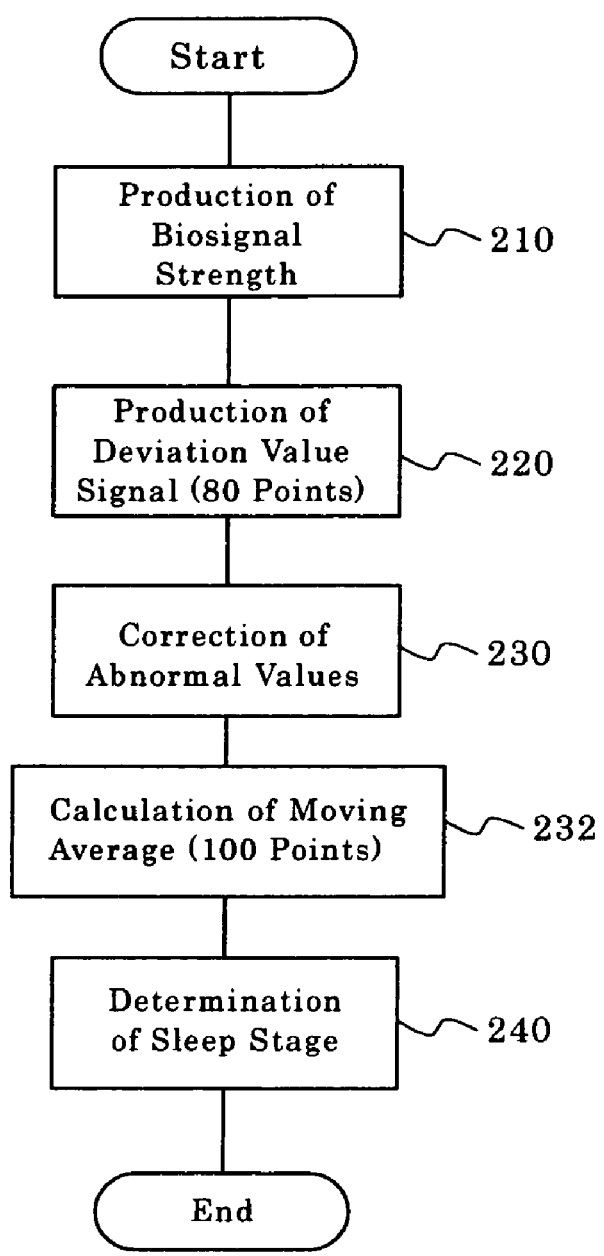
FIG. 4 shows a flowchart illustrating a procedure to determine a sleep stage in a third exemplary embodiment.

FIG. 4 shows a flowchart illustrating the procedure of the third embodiment to determine the sleep stages from the biosignal strength, and is different from the first and second embodiments in that the moving average of the standard deviation is used as the indicator value signal.

For the deviation value obtained by the deviation value calculator 5, the moving average value for 100 consecutive points at each time is calculated (step 232).

Then, using the indicator value signal, the sleep stage is determined in the same way as in the first embodiment (step 240). It is also possible to select whether the correction of the abnormal value is performed or not, if necessary.

In the third embodiment, the moving average value signal is used as the indicator signal. The third embodiment is characterized in that the high frequency component of the signals is consequently removed because of the moving average value and the appearance of the sleep stage for a short time is ignored, whereas the first and second embodiments display the results of the fine sleep stages.

Figure 5:
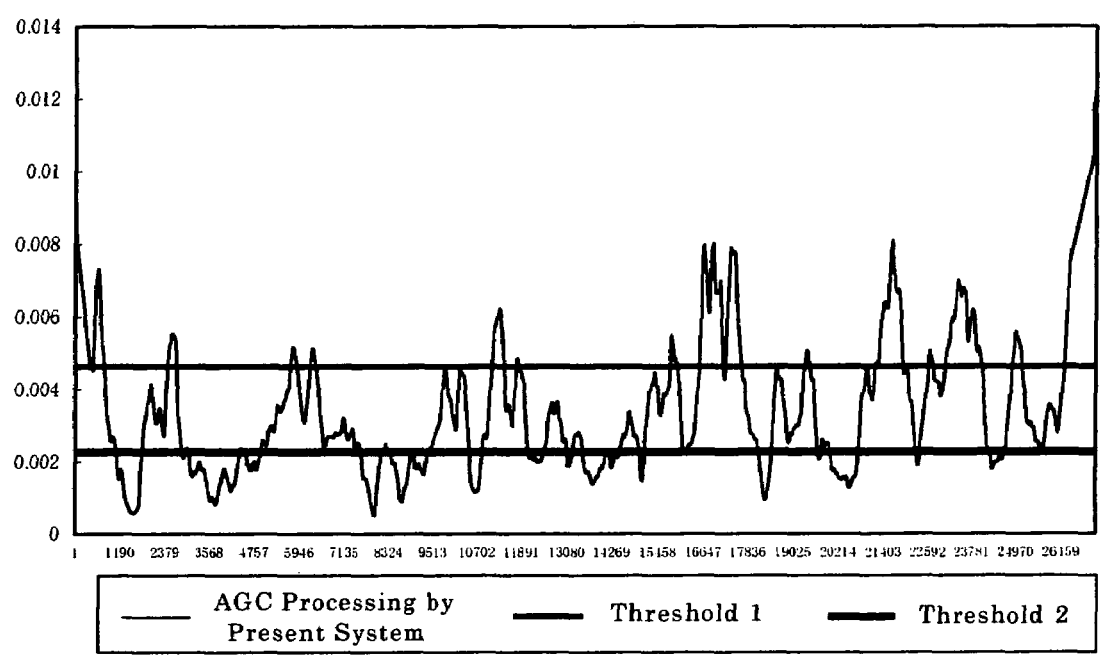
FIG. 5 shows a graph illustrating a relationship between the measurement results of indicator signals and thresholds.

FIG. 5 shows one example of the measurement results of the indicator signals obtained by a system implementing the method of the present invention with AGC processing, and levels of the first and second thresholds. Here, when the value of the indicator signal is above the first threshold (threshold 1), the stage can be determined as the awake/REM sleep stage. When the value of the signal of the difference between the deviation signal and the moving average value is below the second threshold (threshold 2), the stage can be determined as the deep non-REM sleep stage. When it is the level between the first threshold and the second threshold, the stage can be determined as the shallow non-REM sleep.

Figure 6:
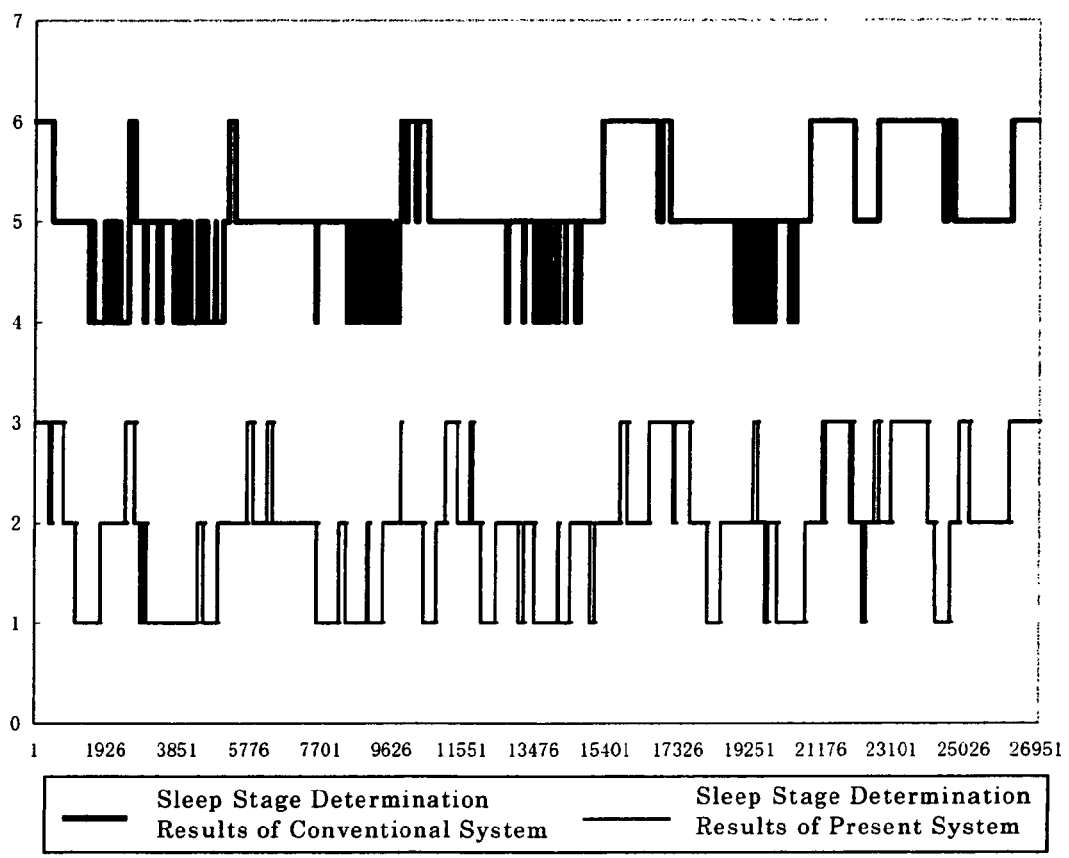
FIG. 6 shows a graph comparing a sleep stage determination result of the present invention with a result of a method using a conventional sleep polysomnogram (PSG).

FIG. 6 shows a comparison of the sleep stage determination results shown in FIG. 5 with the sleep stage determination results obtained by a conventional PSG system. In this measurement comparison example, the coincidence of 86.5% is indicated, and thus the method is practically workable.

In the method for determining the sleep stages of the present invention, it becomes possible to determine the sleep stages of a great number of examinees by one device for realizing the method for determining the sleep stages because the sleep stages can be determined by only analyzing the strength of heartbeat signals. As a result, it becomes possible that the sleep stages of a great number of elderly people in a nursing home are measured for utilization of their health care.

The numbers of the data used in the calculation of the deviation degree and the calculation of the moving average employed in the discussed embodiments are derived as examples, and are not limited thereto.

In the embodiments, the heartbeat signals are detected by extracting from biosignals. In this method, since the high signal strength derived from body movements such as rolling over is included in the data, it is necessary to reduce the effect of body movements, etc., by the use of correction means. However, according to the method for detecting the heartbeat signals by wearing heartbeat rate meter or pulse rate meter, no effect of the body movement is given and it is not necessary to provide correction means. But, it is necessary that the worn heartbeat rate meter or pulse rate meter is small and light enough to avoid physical and mental load.

The method for determining the sleep stages according to the present invention is useful as the method for determining the sleep stage in which the sleep stage is determined from biosignals detected by the biosignal detector 1, and in particular, is suitable for the case of routine use because its handling is simple.

What is claimed is:

1. A method for determining sleep stages of an examinee, the method comprising:
    detecting signals of the examinee with a biosignal detector that is non-restraint, non-contact and non-invasive to the examinee;
    calculating a signal strength with a signal strength calculator obtained as a reciprocal of a coefficient obtained by gain-controlling the detected signals, the gain being set so that an amplitude of the output signals decreases when a peak value of the detected signals exceeds an upper limit threshold and the amplitude of the output signals increases when the peak value of the detected signals is below a lower limit threshold;
    calculating a signal strength variance value that indicates variation of the calculated signal strength; and
    determining a sleep stage by using the signal strength variance value or a value derived from the signal strength variance value as an indicator value.

2. The method for determining sleep stages of an examinee according to claim 1, wherein the indicator value is the signal strength variance value detected in a predetermined time period.

3. The method for determining sleep stages of an examinee according to claim 1, wherein the indicator value is a signal of a difference between the signal strength variance value detected in a predetermined time period and a moving average of the variance value.

4. The method for determining sleep stages of an examinee according to claim 1, wherein the indicator value is a moving average calculated from the signal strength variance value detected in a predetermined time period.

5. The method for determining sleep stages of an examinee according to claim 1, wherein the signal strength variance value obtained by removing abnormal values from the signal strength variance value or a value derived from the signal strength variance value is used as the indicator value.

6. The method for determining sleep stages of an examinee according to claim 1, wherein the biosignal detector comprises:
    a pressure detection tube
    a pressure detection sensor; and
    a biosignal extractor, wherein the biosignal extractor extracts biosignals from a pressure variation detected by the pressure detection sensor.

7. The method for determining sleep stages of an examinee according to claim 1, wherein the biosignal detector is a heartbeat signal detector, such as at least one of an electrocardiograph and a pulse rate meter.

* * * * *